United States Patent
Konya

(10) Patent No.: US 8,690,797 B2
(45) Date of Patent: Apr. 8, 2014

(54) PIERCING SYSTEM

(75) Inventor: Ahmet Konya, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/323,940

(22) Filed: Dec. 13, 2011

(65) Prior Publication Data

US 2012/0316468 A1    Dec. 13, 2012

Related U.S. Application Data

(63) Continuation of application No. PCT/EP2010/003392, filed on Jun. 4, 2010.

(30) Foreign Application Priority Data

Jun. 19, 2009   (EP) ................... 09 008 023

(51) Int. Cl.
    *A61B 5/00*     (2006.01)

(52) U.S. Cl.
    USPC ....................................... 600/583

(58) Field of Classification Search
    USPC ............ 600/583, 347, 309; 606/181; 205/792
    See application file for complete search history.

(56) References Cited

U.S. PATENT DOCUMENTS

| | | | |
|---|---|---|---|
| 6,988,996 B2 | 1/2006 | Roe et al. | |
| 7,476,202 B2 * | 1/2009 | Raney et al. | 600/583 |
| 7,481,777 B2 | 1/2009 | Chan et al. | |
| 7,955,271 B2 | 6/2011 | Roe et al. | |
| 8,000,762 B2 | 8/2011 | Calasso et al. | |
| 2003/0212344 A1 | 11/2003 | Yuzhakov et al. | |
| 2008/0133146 A1 | 6/2008 | Chang et al. | |
| 2008/0200887 A1 | 8/2008 | Haar et al. | |
| 2008/0214917 A1 | 9/2008 | Boecker | |
| 2008/0300509 A1 | 12/2008 | Hoenes et al. | |
| 2009/0099477 A1 | 4/2009 | Hoenes et al. | |
| 2009/0287116 A1 | 11/2009 | Konya | |
| 2009/0321287 A1 | 12/2009 | List et al. | |
| 2010/0198109 A1 | 8/2010 | Harttig | |
| 2010/0286561 A1 | 11/2010 | List et al. | |

FOREIGN PATENT DOCUMENTS

| | | |
|---|---|---|
| CN | 1013853886 | 6/2011 |
| EP | 1 997 429 A1 | 12/2008 |
| EP | 2 050 392 A1 | 4/2009 |
| EP | 2 047 798 B1 | 11/2010 |
| WO | 2005/107596 A2 | 11/2005 |
| WO | WO 2006/076666 A1 | 7/2006 |
| WO | WO 2007/077212 A2 | 7/2007 |
| WO | 2008/083844 A1 | 7/2008 |

\* cited by examiner

*Primary Examiner* — Jeffrey G Hoekstra
*Assistant Examiner* — Fangemonique Smith
(74) *Attorney, Agent, or Firm* — Woodard, Emhardt, Moriarty, McNett & Henry LLP

(57) ABSTRACT

A piercing system has a carrier band carrying piercing elements with test elements disposed in-between. The carrier band holder, which is coupled to a piercing drive, holds a segment of the carrier band and moves together with the segment and a piercing element at the segment during lancing. A wind-up roll displaces the band in a band transport direction. A measuring device measures analyte concentration of a bodily fluid sample received by a test element. A segment of the band having an unused test element is guided past a carrier band segment disposed in the holder or behind the holder in the band transport direction. The two carrier band segments are pressed against each other for transferring the sample from the piercing element to the test element. A method for transferring a bodily fluid sample from a piercing element to a test element is described.

20 Claims, 1 Drawing Sheet

PIERCING SYSTEM

CROSS-REFERENCE TO RELATED APPLICATION

Figure 1:
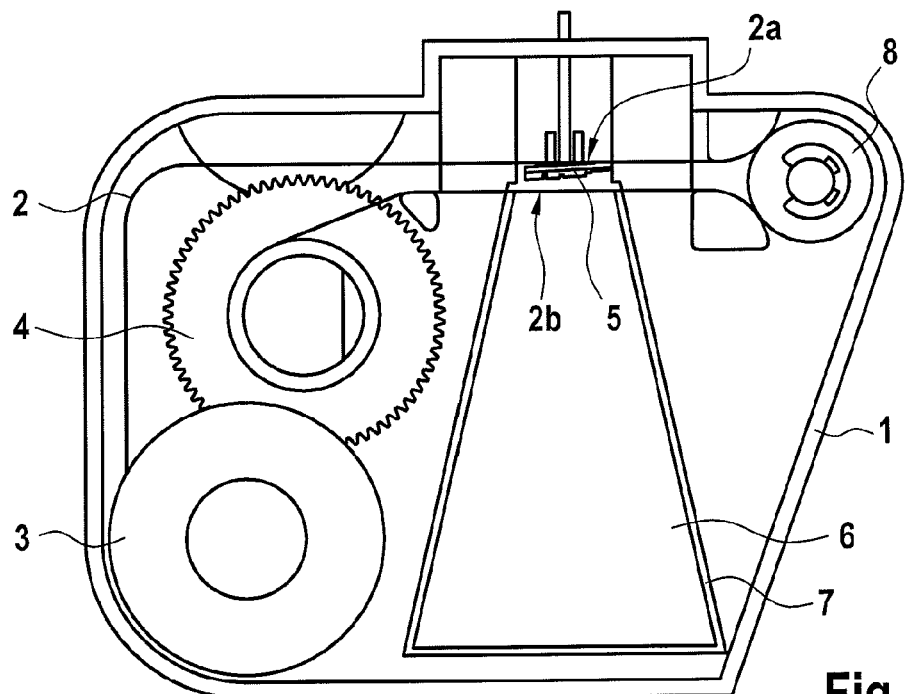

This application is a continuation of International Patent Application No. PCT/EP2010/003392 filed Jun. 4, 2010, which claims the benefit of European Patent Application No. 09008023.5, filed Jun. 19, 2009, the entire disclosures of which are hereby incorporated by reference.

DESCRIPTION

The invention is based on a piercing system having the features specified in the preamble of claim 1.

From WO 2008/083844 A1, a piercing system of this type is known, in which test elements are disposed on a carrier tape, each between piercing elements. To produce a prick, a carrier tape holder, together with a carrier tape segment that contains a piercing element, is moved in the pricking direction. To collect the sample, the carrier tape is transported further, and the carrier tape holder is then moved again in the pricking direction, thereby moving a test element up to a puncture that was produced previously by a piercing element. A disadvantage of this is that for a reliable sample collection, a relatively large sample quantity must be collected from the pricking site.

SUMMARY OF THE INVENTION

An object of the invention is providing a way for improving the user comfort of a piercing system.

This object is solved by a piercing system having the features specified in claim 1, and by a method having the features specified in claim 15. Advantageous refinements of the invention are the subject matter of dependent claims.

In a piercing system according to the invention, a segment of the carrier tape containing an unused test element is guided past a carrier tape segment that is held in the carrier tape holder or downstream of the carrier tape holder in the tape transport direction. To transfer a sample from a piercing element to a test element, these two carrier tape segments are pressed against one another.

When a prick is produced, bodily fluid adheres to a piercing element, and can be used as a sample for determining an analyte concentration, for example, glucose concentration. To increase the volume of bodily fluid obtained in this manner, the piercing element can have a means for holding the sample, for example, depressions, openings, or a capillary channel in the form of a groove or a gap.

By transferring a sample from the piercing element to a test element, an analyte concentration can advantageously be determined within a shorter time, since with a single pricking motion of the carrier tape holder, a prick is produced and a bodily fluid sample is collected. Because in a piercing system according to the invention, a separate discharge of bodily fluid from the pricking site is not necessary, the pricking depth can also be reduced, and therefore a sample can be obtained with less pain.

The test element that receives a sample can be disposed upstream or downstream of the piercing element that delivers the sample, in the direction of tape transport. Preferably, however, the test element that collects the sample is disposed downstream of the piercing element that delivers the sample, in the direction of tape transport, and therefore downstream of the carrier tape holder. Advantageously, the risk of contamination of the carrier tape holder with bodily fluid can thereby be reduced.

In order for a segment of the carrier tape that contains an unused test element to be guided past a carrier tape segment that is held in the carrier tape holder or downstream of the carrier tape holder in the tape transport direction, a tape deflector, for example, a pin or a deflecting roller, may be used, which is disposed between these two carrier tape segments. In this case, one of the two carrier tape segments is guided toward the tape deflector in the tape transport direction, and the other carrier tape segment is guided away from the tape deflector. The two carrier tape segments can thereby be guided along one another, preferably parallel to one another.

In order to press the two carrier tape segments disposed upstream of the wind-up reel against one another, both carrier tape segments can be moved towards one another. However, it is sufficient to move only one of the two carrier tape segments. For example, the carrier tape segment that supports the piercing element can be moved up to the carrier tape segment that supports the test element, and pressed against it.

Before a sample is transferred, the carrier tape may be transported further, so that the piercing element that delivers the sample is no longer held in the carrier tape holder during sample transfer. However, such additional transport is not necessary. The sample is preferably transferred from a piercing element disposed in the carrier tape holder to a test element, because this allows less time to elapse between a pricking and the sample transfer, thereby allowing problems associated with any drying of the sample to be minimized.

An advantageous refinement of the invention provides that the carrier tape holder can be moved transversely to the pricking direction. With a corresponding movement, a used piercing element can be pressed against a test element for transferring a sample. Thereby the carrier tape holder, and therefore the carrier tape segment disposed therein, can be pressed against the carrier tape segment that contains the unused test field.

In a piercing system according to the invention, the piercing elements are preferably oriented transversely to the longitudinal direction, as is the case in the system known from WO 2008/083844 A1. However, it is also possible for the piercing elements to be oriented in the longitudinal direction of the carrier tape, as in the system known from US 2005/0245954 A1.

A piercing system according to the invention is preferably formed by a piercing device and a tape cassette that can be inserted into the piercing device. A tape cassette having a tape course according to the invention is the subject matter of claim 14. Preferably, the carrier tape holder is part of the tape cassette. In this case, as the tape cassette is being inserted into the piercing device, the carrier tape holder can be connected to the piercing drive thereof. It is also possible for the carrier tape holder to be part of the piercing device, and to receive a segment of the carrier tape as the tape cassette is being inserted into the piercing device. Preferably, the tape cassette contains a supply reel, onto which the unused carrier tape is wound. However, the unused carrier tape can also be folded in the tape cassette into a stack. In principle, it is also possible to implement a piercing system according to the invention as a disposable device, in which the carrier tape is not replaceable, and which is disposed of properly once all piercing and test elements disposed on the carrier tape have been used.

DETAILED DESCRIPTION OF THE DRAWINGS

Figure 2:
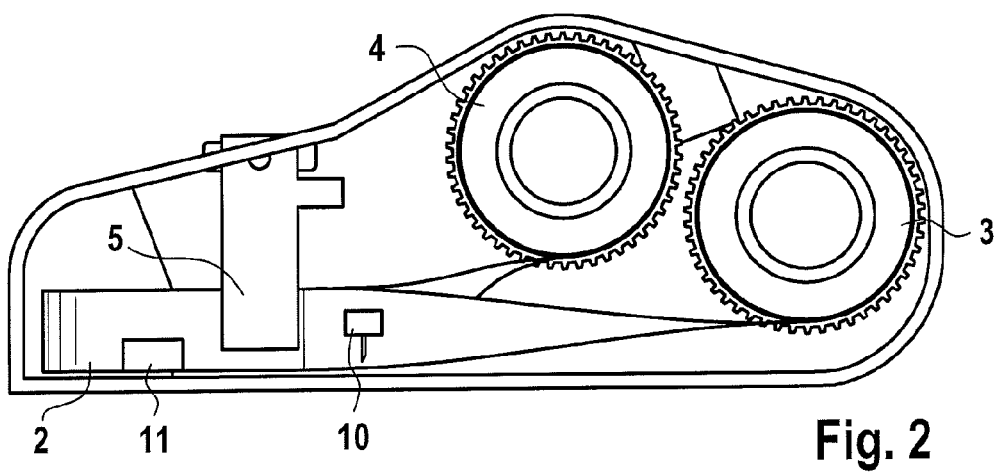

Further details and advantages of a piercing system according to the invention, and of a method according to the invention for transferring a sample of bodily fluid from a piercing element disposed on a carrier tape to a test element disposed on the carrier tape are explained within the context of embodiment examples, with reference to the attached set of drawings. Identical and similar components are identified in the drawings by the same reference signs. The drawings show:

FIG. 1 a schematic illustration of a piercing system according to the invention;

FIG. 2 a schematic illustration of another embodiment example; and

Figure 3:
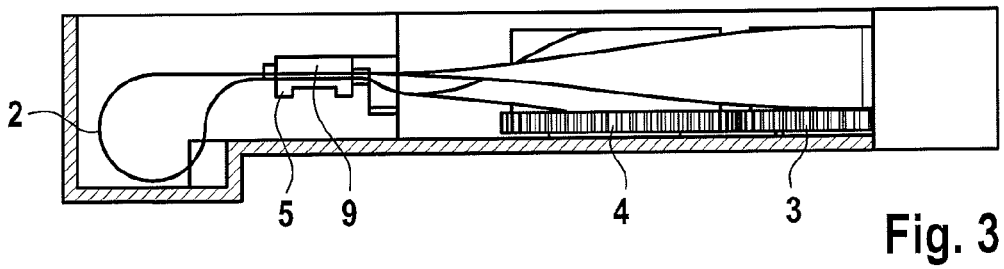

FIG. 3 a side view of FIG. 2.

DETAILED DESCRIPTION

FIG. 1 shows a schematic illustration of an embodiment example of a piercing system, with the device housing 1 opened. In the device housing 1, a carrier tape 2 is disposed, which carries piercing elements and test elements for testing a sample of bodily fluid obtained from a pricking site. The test elements are disposed between the piercing elements. The carrier tape 2 is wound onto a supply reel 3. To allow the piercing elements and the test elements to be used, the carrier tape 2 is gradually unwound from the supply reel 3 and wound onto a wind-up reel 4, which thereby forms a tape transport device.

The carrier tape 2 is guided from the supply reel 3 to a carrier tape holder 5, which is coupled to a piercing drive, not shown in FIG. 1, and holds a segment 2a of the carrier tape 1. To produce a prick, the carrier tape holder 5, together with a piercing element held by the held carrier tape segment 2a, moves in the pricking direction. In the embodiment example shown, the piercing elements are oriented transversely to the longitudinal direction of the carrier tape, and therefore, the pricking direction is perpendicular to the drawing plane of FIG. 1.

The analyte concentration of a sample of bodily fluid obtained from a pricking site can be measured with a measuring device 6. In this, the measuring device 6 cooperates with the test elements, which preferably contain test reagents, for example, for an electrochemical or photometric concentration assay. However, the measuring device 6 can also be provided for a reagent-free concentration assay, for example, via spectroscopic analysis. In the embodiment example shown, the measuring device 6 is embodied for a photometric concentration assay. In this case, test reagents of the test elements cause a concentration-dependent coloration, the intensity of which is measured by the measuring device 6. To minimize stray light, the measuring device 6 has a housing 7, which is enclosed inside the device housing 1.

When a prick is made in a body part of a patient, for example, a finger, which is placed over an opening of the device housing 1, bodily fluid adheres to the piercing element that is used. For the sample of bodily fluid obtained in this manner to be tested, it must be transferred to a test element.

In the embodiment example illustrated here, the carrier tape segment 2b containing an unused test element and a carrier tape segment 2a containing a used piercing element are pressed against one another. In this manner, a piercing element, to which bodily fluid adheres, is placed in contact with a test element, thereby transferring bodily fluid to the test element.

In the embodiment example shown here, the carrier tape segment 2a with the piercing element for delivering the sample is located in the carrier tape holder 5. The carrier tape holder 5 is movable transversely to the pricking direction and transversely to the longitudinal direction of the carrier tape segment 2a held therein. The carrier tape holder 5 can therefore be pressed against a carrier tape segment 2b that is guided past it, in order to transfer the sample. In the embodiment example shown here, the carrier tape holder 5 is thereby also pressed against the measuring device 6, more precisely against the housing 7 thereof. In this manner, a test field can be pressed against the measuring device 6 during a measurement, so that specific conditions for a precise measurement are present. Preferably, the carrier tape holder 5 has an opening on a side opposite the carrier tape segment 2b that contains the test field which receives the sample. Advantageously, the two carrier tape segments 2a, 2b can thereby rest flat against one another during a sample transfer. However, it is sufficient for the carrier tape holder 5 to hold the carrier tape 2 over only a part of its width, and to leave an upper region with the tips of the piercing elements free, so that for transferring the sample, the upper regions of the two carrier tape segments 2a, 2b rest against one another.

In principle, the test element receiving a sample can be disposed upstream or downstream of the carrier tape holder 5 in the tape transport direction. In the embodiment example illustrated here, the test element that receives a sample is disposed downstream of the carrier tape holder 5 in the tape transport direction. In this manner, the risk of contamination of the carrier tape holder 5 with bodily fluid is advantageously avoided.

In the embodiment example illustrated, the carrier tape 2 is guided from the carrier tape holder 5 to a deflecting roller 8 and from there past the carrier tape holder 5 to the wind-up device 4. The carrier tape 2 thereby forms a loop with two carrier tape segments extending along one another, specifically, the carrier tape segment 2a held in the carrier tape holder 5 and a carrier tape segment 2b extending between the carrier tape holder 5 and the measuring device 6. To transfer a sample from a piercing element to a test field, the two carrier tape segments 2a, 2b, which preferably extend approximately parallel to one another, are pressed together, so that the piercing element comes into contact with the test element.

In this, the length of the tape loop is dimensioned according to the distance between a piercing element and the test element assigned to it. However, it is not necessary for the length of the tape loop formed by the deflecting roller 8 to correspond to the distance between a piercing element and the adjacent test element. Specifically, it is also possible for a sample to be transferred from a piercing element not to an adjacent test element, but to a piercing element disposed farther distant, for example, to the piercing element one after the piercing element, or two after the piercing element.

In the simplest case, the carrier tape holder 5 can be embodied as a slit, the width of which always remains constant. Preferably, however, the carrier tape holder 5 has two parts that can be moved in relation to one another, between which the carrier tape 2 is guided. In this manner, the carrier tape holder 5 can hold the carrier tape 2 in a clamping manner between the two parts that are movable relative to one another, during pricking. To allow tape transport, the carrier tape 2 can be released, in other words, the distance between the two parts that are movable relative to one another can be increased, so that when there is low tape friction, the next piercing element can be brought to its position of use in the carrier tape holder 5 by winding up the wind-up reel 4. For example, the two parts of the carrier tape holder 5 that are movable relative to one another can be pivotable. The cooperating legs of a pair of pliers are also moved according to this principle to hold something in a clamping manner.

Preferably, no tape transport occurs between a pricking and a sample transfer to a test element, i.e., the wind-up reel 4 is not moved between a pricking and a sample transfer. The position of use of a piercing element in the carrier tape holder 5 during pricking is therefore preferably also used for transferring a sample.

The movement of the carrier tape holder 5 for the purpose of pressing the two carrier tape segments 2a, 2b together during a sample transfer is preferably effected automatically by the piercing drive, following a pricking movement. For example, the piercing drive can have a suitable link motion for this purpose. Specifically, it is advantageous for a sample to be transferred as soon as possible by a piercing element to a test element. Particularly when the surrounding air is dry, the danger exists that bodily fluid will be evaporated and a sample will dry on the piercing element, and therefore, a sample transfer is possible only within a short window of time.

FIGS. 2 and 3 show a further embodiment example with the device housing 1 open, in a schematic plan view and an associated side view, in which the piercing drive 9 is also shown coupled to the carrier tape holder 5. The difference from the above-described embodiment example consists essentially in that the carrier tape 2 undergoes a quarter turn on its path from the supply reel 3 to the carrier tape holder 5. Therefore, the geometric rotational axis of the supply reel 3 is not oriented parallel to the pricking direction, as in the embodiment example described above, and is instead oriented transversely thereto.

Between the measuring device 6 and the wind-up reel 4, the carrier tape 2 is twisted another quarter turn. The geometric rotational axis of the wind-up reel 4 is therefore oriented parallel to the geometric rotational axis of the supply reel 3. The second quarter turn of the carrier tape 2 can reverse the preceding quarter turn, or can add to it so that overall, the carrier tape 2 is twisted one-half turn.

In FIG. 2, the piercing elements 10 and test elements 11 not shown in FIG. 1 are clearly identified on the carrier tape 2. The piercing elements 10 can be made of metal, particularly steel, however, other materials such as plastic or ceramic may also be used. The piercing elements 10 have a sample receiving means, which can be embodied, for example, as a capillary channel or as depressions or openings, in which bodily fluid adheres when a prick is made. A capillary channel is a channel in which bodily fluid is held by capillary forces when a prick is made. A channel of this type can be embodied as a groove or can be a slit, which is open to the upper and lower sides of the piercing element 10.

The test elements 11 can be provided as test fields on the carrier tape 2. The test elements 11 have an absorbent surface, in order to facilitate sample collection from a piercing element 10. The absorbent surface can be formed, for example, by applying a paste or a non-woven fabric, and can contain test reagents. For a photometric concentration assay, it can be advantageous to use a transparent carrier tape 2, so that measuring light is able to pass through the carrier tape 2. It is also possible to glue test elements to properly sized windows in the carrier tape 2.

List Of Reference Numbers
  1 Device housing
  2 Carrier tape
  2a Carrier tape segment
  2b Carrier tape segment
  3 Supply reel
  4 Wind-up reel
  5 Carrier tape holder
  6 Measuring device
  7 Housing
  8 Deflecting roller
  9 Piercing drive
  10 Piercing element
  11 Test element

The invention claimed is:

1. A piercing system comprising
   a carrier tape, which carries piercing elements and test elements for testing a sample of bodily fluid obtained by pricking, the test elements being disposed between the piercing elements, wherein the piercing elements each have a sample receiving means configured to receive the sample,
   a piercing drive for causing a pricking movement of piercing elements,
   a carrier tape holder coupled to the piercing drive and holding a segment of the carrier tape, the carrier tape holder moving, together with this segment and a piercing element carried by the segment, in the pricking direction during pricking,
   a wind-up reel, for moving the carrier tape by winding in a tape transport direction,
   a measuring device for measuring an analyte concentration in a sample of bodily fluid collected by a test element,
   a guide configured to guide a segment of the carrier tape having an unused test element past a carrier tape segment, which is disposed in the carrier tape holder or behind the carrier tape holder in the tape transport direction, and
   wherein the carrier tape holder is configured to press said two carrier tape segments against one another for transferring a sample from the piercing element to the test element.

2. The piercing system according to claim 1, characterized in that the two carrier tape segments are pressed against one another during a measurement.

3. The piercing system according to claim 1, characterized in that the carrier tape between the two carrier tape segments that are pressed against one another for transferring a sample forms a loop.

4. The piercing system according to claim 1, characterized in that the guide includes a deflecting roller configured to guide the carrier tape between the two carrier tape segments that are pressed against one another for transferring the sample.

5. The piercing system according to claim 1, characterized in that the test element configured to receive the sample is disposed ahead of the piercing element configured to transfer the sample on the carrier tape in the tape transport direction.

6. The piercing system according to claim 1, characterized in that the carrier tape holder is configured to move the carrier tape segment that carries the piercing toward a tape segment that carries a test element.

7. The piercing system according to claim 1, characterized in that the piercing element is disposed in the carrier tape holder to transfer the sample to the test element.

8. The piercing system according to claim 1, characterized in that the carrier tape holder is movable transversely to the pricking direction, to allow a used piercing element to be pressed against a test element for transferring a sample.

9. The piercing system according to claim 1, characterized in that the piercing elements are oriented transversely to the longitudinal direction of the carrier tape.

10. The piercing system according to claim 1, characterized in that the carrier tape holder has two parts that are movable relative to one another, between which the carrier tape passes.

11. The piercing system according to claim 10, characterized in that during a pricking, the carrier tape holder is configured to clamp the carrier tape between the two parts that are movable relative to one another.

12. The piercing system according to claim 1, characterized in that the piercing drive is configured to press the carrier tape against the measuring device during a measurement.

13. The piercing system according to claim 12, characterized in that the carrier tape holder is configured to press the carrier tape against the housing of the measuring device.

14. A tape cartridge for a piercing system, comprising:
a carrier tape, which carries piercing elements and test elements disposed between the piercing elements, for testing a sample of bodily fluid obtained by a prick, wherein the piercing elements each have a sample receiving means configured to receive the sample,
a wind-up reel for winding up the carrier tape, and
a guide configured to guide two carrier tape segments past one another, so that, to transfer a sample from a piercing element to a test element, these two carrier tape segments can be pressed against one another.

15. A method, comprising:
guiding a carrier tape around a tape deflection, which is disposed between a carrier tape segment that carries a piercing element and a carrier tape segment that carries a test element, wherein the piercing element has a sample receiving means configured to receive the sample;
pressing the two carrier tape segments together such that the piercing element comes into contact with the test element; and
transferring a sample of bodily fluid from the sample receiving means of the piercing element to the test element.

16. The piercing system according to claim 1, further comprising:
a supply reel around which the carrier tape is wrapped.

17. The piercing system according to claim 16, wherein the carrier tape is twisted by a quarter turn between the supply reel and the carrier tape holder.

18. The piercing system according to claim 17, wherein the carrier tape is twisted by a quarter turn between the carrier tape holder and the wind-up reel.

19. The method of claim 15, wherein:
the tape deflection includes a deflecting roller; and
said guiding includes looping the carrier tape around the deflecting roller.

20. The method of claim 15, further comprising:
performing a pricking movement with the piercing element that includes a sample receiving means; and
adhering the sample to the sample receiving means of the piercing element.

* * * * *